(12) United States Patent
Bradley et al.

(10) Patent No.: US 7,786,335 B2
(45) Date of Patent: Aug. 31, 2010

(54) METHOD FOR PREPARING 1,1,1,3,3-PENTAFLUOROPROPANE

(75) Inventors: David E. Bradley, Buffalo, NY (US); David Nalewajek, West Seneca, NY (US); Robert L. Bell, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/263,848

(22) Filed: Nov. 3, 2008

(65) Prior Publication Data

US 2009/0149681 A1    Jun. 11, 2009

Related U.S. Application Data

(63) Continuation of application No. 11/284,379, filed on Nov. 21, 2005, now abandoned.

(51) Int. Cl.
    *C07C 17/00*      (2006.01)
(52) U.S. Cl. ........................................ 570/167; 570/168
(58) Field of Classification Search ................. 570/167, 570/168
See application file for complete search history.

(56) References Cited

U.S. PATENT DOCUMENTS

| | | | |
|---|---|---|---|
| 5,496,866 A | 3/1996 | Sommerfeld et al. | |
| 5,574,192 A | 11/1996 | VanDerPuy et al. | |
| 5,710,352 A | 1/1998 | Tung | |
| 5,895,639 A | 4/1999 | Swain et al. | |
| 5,902,912 A | 5/1999 | Tung et al. | |
| 5,969,198 A | 10/1999 | Thenappan et al. | |
| 6,001,796 A | 12/1999 | Pham et al. | |
| 6,080,899 A | 6/2000 | Bradley et al. | |
| 6,111,150 A | 8/2000 | Sakyu et al. | |
| 6,198,010 B1 | 3/2001 | Yoshikawa et al. | |
| 6,235,951 B1 | 5/2001 | Sakyu et al. | |
| 6,291,728 B1 | 9/2001 | Aoyama et al. | |
| 6,316,681 B1 | 11/2001 | Yoshikawa et al. | |
| 6,403,847 B1 * | 6/2002 | Nakada et al. | 570/156 |
| 6,846,963 B2 | 1/2005 | Nakada et al. | |

* cited by examiner

*Primary Examiner*—Jafar Parsa
(74) *Attorney, Agent, or Firm*—Bruce O. Bradford

(57) ABSTRACT

A process for the production of C2-C4 hydrofluorocarbon, such as 1,1,1,3,3-pentafluoropropane, by contacting a non-fluorinated hydrochlorocarbon with a fluorinating agent, such as hydrogen fluoride, in a liquid catalyst system preferably comprising fluorinated superacid catalyst prepared from $SbF_5$, $NbF_5$, $TaF_5$ or $TaF_5/SnF_4$ and HF.

21 Claims, 1 Drawing Sheet

METHOD FOR PREPARING 1,1,1,3,3-PENTAFLUOROPROPANE

CROSS REFERENCE TO RELATED APPLICATION

This application is a continuation of U.S. application Ser. No. 11/284,379, filed Nov. 21, 2005, which is incorporated herein by reference.

BACKGROUND OF THE INVENTION

1. Field of the Invention

The present invention relates to method of producing hydrofluorocarbons, and particularly lower alkyl hydrofluorocarbons, from hydrochlorocarbons.

2. Description of Related Art

It is known that when certain halocarbons are released into the atmosphere, they undergo reactions that result in the depletion of the Earth's ozone layer. Examples of environmentally harmful halocarbons include certain hydrochlorocarbons (HCCs), hydrochlorofluorocarbons (HCFCs), and chlorofluorocarbons (CFCs). One such CFC is trichlorofluoromethane (CFC-11), a compound that conventionally has been used in foam insulation applications. Due to CFC-11's potential for environmental damage, replacements for this compound have been sought. One proposed substitute for CFC-11 in foaming application is 1,1-dichloro-1-fluoroethane (HCFC-141b). Although HCFC-141b also adversely affects the ozone layer, its impact is significantly less than that of CFC-11.

Certain lower alkyl hydrofluorocarbons, including the compound 1,1,1,3,3-pentafluoropropane (HFC-245fa), have been identified as a potential replacements for HCFC-141b in a variety of applications, most notably insulation and refrigeration applications. HFC-245fa has good insulation characteristics, low toxicity, correct vapor pressure and low flammability properties. Accordingly the demand for HFC-245fa has grown and as well as a need for more economical means of producing compounds such as HFC-245fa.

Methods for producing hydrofluorocarbons (HFCs) by reacting hydrogen fluoride (HF) with various hydrochlorocarbon and/or hydrochlorofluorocarbon compounds are known. For example, various schemes for producing HFC-245fa from 1,1,1,3,3-pentachloropropane (HCC-240fa) or 1,3,3,3-tetrachloro-1-propene (HCC-1230) and hydrogen fluoride (HF) either in the liquid or vapor phase have been described. See, for example, U.S. Pat. Nos. 5,902,912 and 5,710,352. For liquid phase processes, a catalyst such as SbCl$_5$ or SbF$_3$Cl$_2$ is usually required to promote the exchange of chlorine atoms on the organic reactant with fluorine atoms of the hydrogen fluoride reactant. Unfortunately, the reaction conditions (e.g. reactant and catalyst concentrations, temperatures, pressures and the need for oxidants such as chlorine to maintain catalyst activity) required to promote this halogen exchange process can be extremely corrosive to metals commonly used for liquid phase reactors, such as Monel, Inconel and Hastelloy C. As a result of the extremely corrosive reaction environment most reactors used for fluorination processes must be lined with fluoropolymers. However, these lined reactors suffer from poor heat transfer and HF permeation of the liner. In addition, the use of Cl$_2$ as an oxidant results in a yield loss due to chlorination of various raw materials, intermediates, and reactants.

SUMMARY OF THE INVENTION

Applicants have discovered advantageous methods for preparing alkyl hydrofluorocarbons, such as C2-C4 hydrofluorocarbons, and preferably HFC-245fa. In preferred embodiments the methods include liquid phase reactions which overcome many of the disadvantages of prior processes, including the many of the problems mentioned herein.

In one preferred aspect, applicants have discovered that HFC-245fa can be employed as a solvent for a superacid system in which HFC-245fa can also be prepared at commercially viable production rates and under conditions that are not corrosive to metals such as Hastelloy C. The preferred methods of the present invention utilize a reaction system (eg., reactants, solvent, acid, and catalyst) capable of achieving low to negligible corrosion rates with respect to certain metals and alloys, while also achieving productivities (defined as amount of product made per unit of time per unit volume of reaction mass) equal to or greater than systems which employ corrosive "conventional" halide exchange liquid phase reaction systems (e.g. high concentration SbCl$_5$). The preferred method and systems of the present invention can thus utilize reactors constructed with contact materials having greater heat transfer rates (eg., metals) as compared to fluoropolymer lined reactors which are necessitated by the highly corrosive conventional liquid phase reaction systems. In addition, the preferred aspects of the present invention can be in the form of continuous production methods and systems using equipment configurations similar to those currently employed in the production of other HCFC and HFC compounds such as chlorodifluoromethane (HCFC-22), 1,1-dichloro-1-fluoroethane (HCFC-141b), and 1,1,1-trifluoroethane (HCFC-143a).

According to preferred aspects of the present invention, at least one non-fluorinated hydrochlorocarbon, such as HCC-240fa and/or HCC-1230, is added to a solution comprising: (a) a solvent (preferably C2-C4 hydrofluorocarbon solvent, more preferably C3 hydrofluorocarbon solvent, and even more preferably HFC-245fa solvent); (b) a fluorinating agent (such as HF); and (c) a fluorination catalyst, such as a metal pentafluoride under conditions effective to produce the desired C2-C4 hydrofluorocarbon reaction product, preferably HFC-245fa.

Although not wanting to be bound to any particular theory, it is thought that when a fluorinating agent, particularly HF, reacts in the presence of metal halide catalyst, such as SbF$_5$, TaF$_5$, and NbF$_5$, an exothermic reaction occurs to form a superacid system. It is believed that this reaction may occur according to the following reaction scheme:

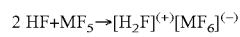

$$2\,HF + MF_5 \rightarrow [H_2F]^{(+)}[MF_6]^{(-)}$$

The higher Lewis acidity of super-acids such as anhydrous hexafluoroantiminic acid (HSbF$_6$), anhydrous hexafluorotantalic acid (HTaF$_6$), or anhydrous hexafluoroniobic acid (HNbF$_6$) relative to conventional acid catalysts such as "HSbCl$_5$F" and "HSbF$_4$Cl$_2$" (as measured by the Hammet scale) allow for lower concentrations of catalyst to be employed while still achieving similar productivity. In addition, the reaction mechanism may be different than the "Swarts" reaction based systems which are presumably dominant under conditions of high SbCl$_5$ concentration and low HF concentration. Moreover, compared to conventional acid catalysts, fully fluorinated superacids require much less, if any, oxidants (such as chlorine) to maintain their activity, thus further lowering yield losses due to the presence of $Cl_2$ in the reaction system and further lowering the corrosive tendency of the reaction system. The corrosion of reactors which use lower concentrations of fully fluorinated superacid catalyst is considerably less compared to conventional high $SbCl_5$ concentration system. The latter has been demonstrated to be very corrosive to metals such as Hastelloy C and Monel 400. Also, the low catalyst concentration system of certain preferred aspects of the present invention has other benefits, such as the low viscosity and the presence of only one liquid phase in the reactor.

One preferred aspect of the present invention provides methods of producing C2-C4 hydrofluorcarbons, preferably 1,1,1,3,3-pentafluoropropane, comprising: (a) providing a solution comprising a metal halide fluorination catalyst at least partially dissolved in an azeotrope-like mixture of 1,1,1,3,3-pentafluoropropane and hydrogen fluoride; and (b) adding to the solution at least one non-fluorinated HCC to form a liquid reaction system under conditions effective to convert at least a portion, and preferably a substantial portion, of said non-fluorinated HCC (preferably by reaction of said HCC with said HF) to the desired C2-C4 hydrofluorcarbon, preferably 1,1,1,3,3-pentafluoropropane.

In certain preferred embodiments, the present invention provides a continuous process for the preparation of HFC-245fa which comprises continuously introducing a stream comprising C3 hydrochlorocarbon, preferably 1,1,1,3,3-pentachloropropane, 1,3,3,3-tetrachloro-1-propene or combinations of these into a reactor containing a solution of HFC-245fa, HF, and a metal halide fluorination catalyst selected from the group consisting of $SbF_5$, $NbF_5$, $TaF_5$ and mixtures of $TaF_5$ and $SnF_4$ under conditions which produce HFC-245fa. Preferably the process also includes the step of introducing anhydrous hydrogen fluoride into said reaction system.

DETAILED DESCRIPTION OF PREFERRED EMBODIMENTS

Figure 1:
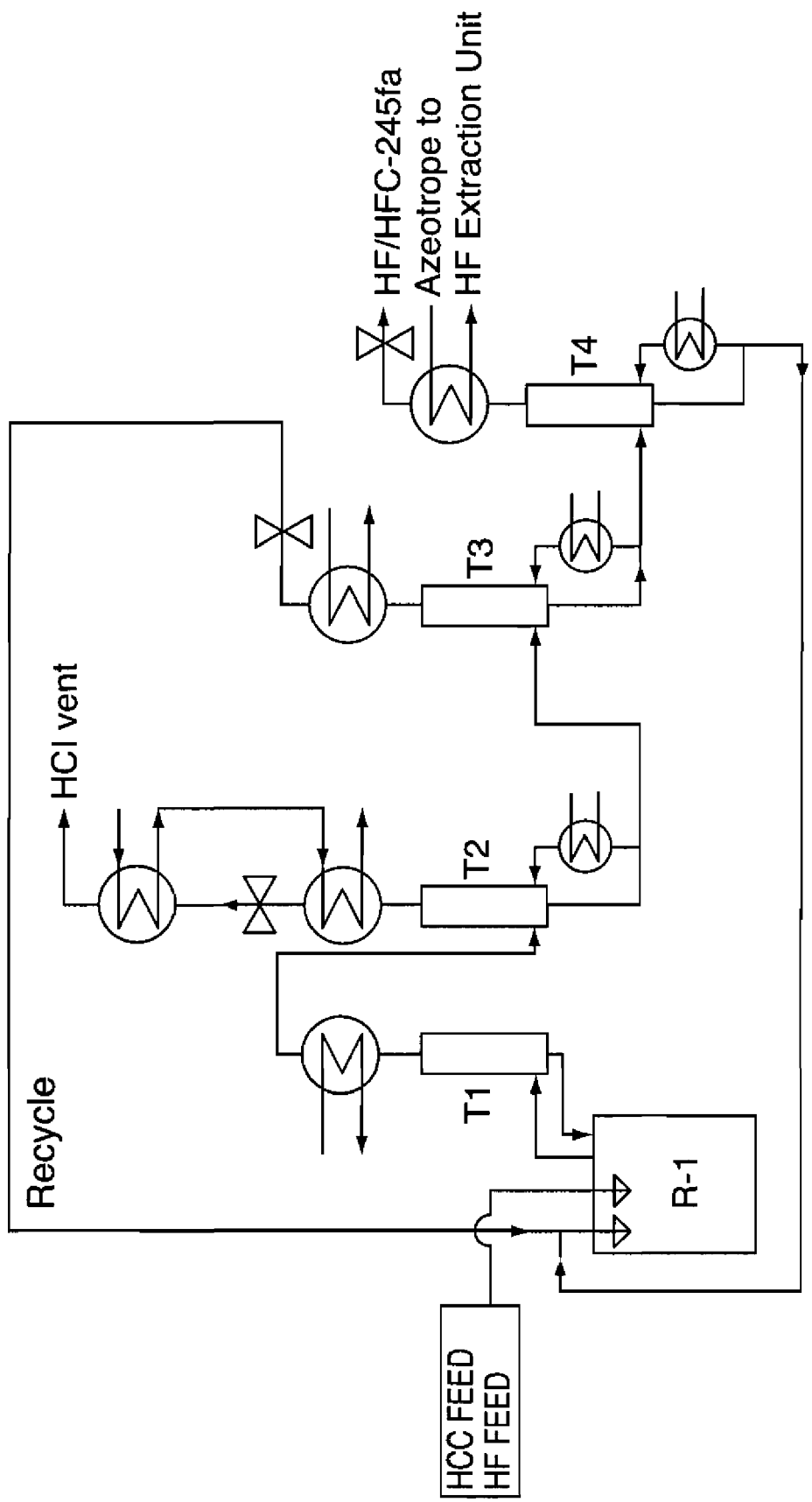
FIG. 1 depicts a schematic representation of an embodiment of the present invention wherein a desired HFC (such as HFC-245fa) is produced via a continuous process.

Preferred aspects of the present invention provide for the catalytic, liquid phase fluorination of at least one non-fluorinated hydrochlorocarbon, such as HCC-240fa, HCC-1230, or a mixture of HCC-240fa and HCC-1230, with HF, wherein the reaction product and the solvent for the reaction are both HFC-245fa. In certain embodiments of the invention, a solution of HFC-245fa, HF and catalyst is first prepared in a fluorination reactor. The reactor according to such preferred aspects of the invention may be any suitable fluorination reaction pressure vessel or autoclave which is constructed from materials that are resistant to the corrosive effects of hydrogen fluoride at the temperatures and pressures of the reaction, such as Hastelloy C, Monel, Inconel, Molybdenum or fluoropolymer lined steel. After this solution is prepared and the reactor is brought to the desired temperature and pressure, the hydrochlorocarbon and HF are fed into the reactor, preferably substantially simultaneously.

Preferred liquid phase metal halide catalysts for this reaction are $SbF_5$, $NbF_5$, $TaF_5$, mixtures of $TaF_5$ and $SnF_4$, and some combination thereof. At the preferred concentrations and temperatures employed in this reaction, the HFC-245fa, HF, and catalyst are preferably completely, or at least mostly, miscible. The exothermic reaction between the HF and metal halide preferably occurs to form a superacid, presumably according to the following scheme:

$$2\ HF + MF_5 \rightarrow [H_2F]^{(+)}[MF_6]^{(-)}$$

The reaction mixture is then preferably brought to reaction temperature and pressure conditions such that the HF/HFC-245fa azeotrope-like composition is formed, and preferably begins to reflux.

As used herein the term "azeotrope-like" refers, in a broad sense, to compositions that are strictly azeotropic and compositions that behave like azeotropic mixtures. From fundamental principles, the thermodynamic state of & fluid is defined by pressure, temperature, liquid composition, and vapor composition. An azeotropic mixture is a system of two or more components in which the liquid composition and vapor composition are equal at the state pressure and temperature. In practice, this means that the components of an azeotropic mixture are constant boiling and cannot be separated during a phase change.

Thus, "azeotrope-like" compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree.

Another characteristic of azotrope-like compositions is that there is a range of compositions containing the same components in varying proportions that are azeotrope-like or constant boiling. All such compositions are intended to be covered by the terms "azeotrope-like" and "constant boiling". For example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

The reactor in accordance with preferred aspects of the present invention is preferably maintained at a temperature of from about 60° C. to 120° C., more preferably from about 70° C. to 110° C., and even more preferably from about 80° C. to 100° C. The reactor pressure is preferentially maintained at the vapor pressure of the HF/HFC-245fa azeotrope-like composition, which is largely determined by the temperature of the reactor system as well as its composition. The HF/HFC-245fa azeotrope-like vapor pressure characteristics and compositions are described in U.S. Pat. No. 6,001,796, which is incorporated herein by reference.

Preferred non-fluorinated hydrochlorocarbons include, HCC-240fa, HCC-1230, and combinations thereof. Without being bound by or to any particular theory of operation, it is believed that when these reactants are used the overall net reactions are as follows:

HCC-240fa $CCl_3$—$CH_2$—$CH_2Cl$+5 HF→$CF_3$—$CH_2$—$CF_2H$+5HCl

HCC-1230 $CCl_3$—CH=CHCl+5 HF→$CF_3$—$CH_2$—$CF_2H$+4HCl

During the latter parts of the reactions, it is believed that certain volatile intermediates are formed which can be separated from the reaction product and returned back to the reactor in order to be converted into the HFC-245fa product, which has a boiling point of 15° C. at 1 atmosphere of pressure. These intermediates include, but are not limited to, the following compounds:

1,3,3,3-tetrfluoro-1-chloropropane (HCFC-244) nbp=39° C.

3,3,3-trifluoro-1-chloropropene (HCFC-1233) nbp=21° C.

1,3,3,3-tetrafluoro-1-propene (HFC-1234) nbp=−19° C.

The preferred net molar feed ratio of HF to HCC (preferably HCC-240, HCC-1230, or some combination thereof) is from about 3:1 to about 8:1, more preferably from about 4:1 to about 6:1, and even more preferably in certain embodiments about 5:1. Since some HF may be lost from the reaction system via carryover with the HCl byproduct, this loss is preferably compensated for by raising the feed ratio accordingly. A significantly higher ratio could result in the gradual accumulation of HF in the reactor, while a significantly lower net ratio could result in the gradual depletion of HF in the reactor. Of course, the exact amount of HF in the feed can be controlled by monitoring the amount of HF in the reaction product in accordance with known techniques.

Preferably, the mole ratio of HF to HCC-230 and/or HCC-1230 in the reaction system is greater than about 10:1. The mole ratio of HF:HFC-245fa in the reactor is preferably not more than about 12:1, more preferably not more than about 8:1, and most preferably about 6:1.

The amount of catalyst in the reactor can vary within the broad scope of the present invention depending upon numerous factors, including the trade-off between increased production and the potential increase in corrosion. The amount of catalyst preferably ranges from about 0.5 wt % to about 10 wt % of the starting mixture, more preferably from about 1 wt % to about 5 wt % and most preferably from about 2 wt % to about 4 wt %. The molar ratio of HF to catalyst initially present and prior to the HCC addition is preferably at least about 10:1, more preferably at least about 20:1, and even more preferably at least about 40:1. The amount of HFC-245fa solvent present in the reaction mixture at steady state preferably ranges from about 40 to about 80 wt %, more preferably from about 45 to about 70 wt %, and even more preferably from about 50 to about 60 wt %.

In certain preferred embodiments, the solvent is put into the reaction vessel at startup and preferably maintained within acceptable levels, which in preferred embodiments is substantially constant amount, by removal of HFC-245fa as it is generated. Due to the azeotrope-like composition formed by HF and the product/solvent, any HF lost is preferably replaced by additional HF input. This loss can arise when a portion of the HF/HFC-245fa azeotrope-like composition is removed from the reactor so that at least a part of the HFC-245fa can be separated as a product. Any suitable means can be used to separate HFC-245fa from the azeotrope-like composition, including the extraction of HF from the azeotrope-like composition by concentrated sulfuric acid. HFC-245fa has very limited miscibility in $H_2SO_4$ relative to HF, and the resulting HF—$H_2SO_4$ solution can be heated to distill off the HF, which can then be returned to the reactor as a recycle stream.

The preferred feed rate of HCC-240fa or HCC-1230 ranges from about 0.1 to about 10 lbs/gallon-hour based upon the total volume of liquids in the reactor. A more preferred range is from about 1 to about 5 lbs/gallon-hour, while the most preferred range is from about 2 to about 4 lbs/gallon-hour.

In certain preferred embodiments, the unreacted hydrochlorocarbons, such as HCC-230, and partially fluorinated intermediates are volatilized from the liquid reaction mixture, along with HF and the HF/HFC-245fa azeotrope-like composition, and then recycled back to the to the reactor for further fluorination. In general, almost all of the intermediates are less volatile than the product, and therefore this recycle of higher boiling materials (with the exception of HFC-1234) is easily effected by fractional distillation techniques well known to those skilled in the art.

This continuous production process can utilize several features of existing liquid phase HF reaction processes, including a pressure reactor connected to a continuous fractional distillation column or series of columns. FIG. 1 depicts one preferred embodiment of this invention wherein a reactor is maintained at a constant level and composition by feeding HF, chlorinated feed and recycled organics into the reaction vessel R-1 at a rate that the chlorinated materials will be converted into the desired product, such as the preferred HFC-245fa. In addition to the HF and organic feeds, small amounts of desiccants, such as $SOCl_2$, $COCl_2$ or $COF_2$ may be added in order to remove any trace amounts of water that would enter the reaction system. For example, HF may contain 500 ppm $H_2O$, which, over time, can accumulate in the reboiler if not removed (e.g. by a reaction that consumes the water molecules). The vapor outputs from the reactor, consisting mostly of HCl, the HF/HFC-245fa azeotrope-like composition, and various smaller amounts of intermediates and feedstock, are preferably directed to a fractional distillation column T-1, where most of the higher boiling compounds are condensed/refluxed back to the reactor. The vapor stream leaving the partial condenser of T-1 is then preferably fed to another column T-2, under conditions so that the by-product HCl is refluxed and vented off for either collection or neutralization. The higher boiling materials from the reboiler of column T-2 can then be fed to another column T-3, wherein the remaining trace intermediates, such as HFC-1234, are preferably distilled-off and recycled back to the reactor, while higher boiling compounds that accumulate are preferably then fed to column T-4. In this T-4 distillation column, when present, the HFC-245fa/HF azeotrope-like composition (which generally comprises from about 22 wt % HF/88 wt % HFC-245fa) is preferably distilled off and transferred to the HF extraction unit while the accumulated higher boiling compounds such as HCFC-244 and HCFC-1233 are fed back to the reactor, preferably at rates equal to their accumulation. The HF/HFC-245fa vapor stream leaving the top of T-4 (via the partial condenser) is then preferably fed to an HF extraction column, where the HF present in the vapor azeotrope-like composition is extracted by a fluid such as sulfuric acid or fluorosulfonic acid. The crude HFC-245fa is then collected and, if desired, further purified to yield the desired product.

In many preferred embodiments it is highly desired that the catalyst and the HCC material(s) not be allowed to contact each other except in the presence of a molar excess of HF in order to inhibit or substantially prevent catalyst deactivation. Such a deactivation may occur by a process known as the Swarts reaction, resulting in a chlorinated metal halide that possesses a significantly lower (Lewis) acidity, as measured via the Hammet scale. An example of the undesired Swarts reaction would be as follows:

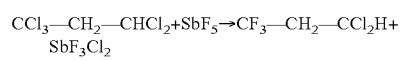

In contrast, the preferred reaction mechanism according to the present invention is believed to be represented as follows:

R—Cl+[H$_2$F][SbF$_6$][R$^{(+)}$][SbF$_6$]$^{(-)}$+HCl+HF

[R$^{(+)}$][SbF$_6$]$^{(-)}$+2HF→R—F+[H$_2$F][SbF$_6$]

The HCl byproduct is preferentially vented off from the system and either condensed with a low temperature coolant in a second distillation system, or neutralized with an appropriate base such as NaOH or CaCO$_3$. If the HCl by-product is to be neutralized, the high pressure gas (at a range of 100 to 300 psig) can be used as a source of refrigeration as it is expanded from the cold high pressure state to atmospheric pressure. This would reduce the energy consumption of the process, as there is a considerable amount of HCl made from the conversion of HCC-240 into HFC-245fa (1.36 lbs HCl/lb HFC-245fa).

The present mechanism differs from the Swarts reaction, even though the end result is similar. The Swarts reaction, which can take place even in the absence of HF, occurs as follows:

$R\text{-Cl} + SbF_{(5-x)}Cl_{(x)} \rightarrow [R^{(+)}][SbF_{(5-x)}Cl_{(x+1)}^{(-)}]$ $\rightarrow R\text{-F} + SbF_{(4-x)}Cl_{(x+1)}$ $x = 0, 1, 2, 3$ or $4$ In practice, the Swarts catalyst can be regenerated with HF:

Sb$_{(4-x)}$Cl$_{(x+1)}$+HF→SbF$_{(5-x)}$Cl$_{(x)}$+HCl

The by-product HCl formed, is easily distilled away from the re-generated Swarts catalyst due to its low boiling point (nbp=−83° C.) versus the normal boiling point of HF (nbp=+20° C.). This catalyst can also decompose into the +3 valency by eliminating Cl$_2$; for example:

SbF$_3$Cl$_2$→SbF$_3$+Cl$_2$

This is a temperature related equilibrium reaction (increasing dramatically as the temperature rises from 75° C.) that needs to be reversed by the addition of Cl$_2$ into the reaction system. The Sb$^{+3}$ halides are ineffective as halogen exchange catalysts with HCCs/HFCs.

According to certain preferred embodiments, the reaction process has a first step wherein a carefully maintained ratio of HF to HCC (such as HCC-240fa, HCC-1234 or combinations of these) is fed into a reactor after a HFC-245fa/HF/catalyst system is refluxing at the correct temperature and pressure, for example in column T-1. As the system approaches steady state, recycled organic feeds and recycled HF can be sent back to the reactor; as this occurs, the HF:organic feed ratio can be trimmed back to a mole ratio of about 5:1. This method is preferred because the vapor exiting the initial column would contain HCl, HFC-245fa, and HF in a molar ratio of approximately 5:1:1.68, and thus depleting the HF in the reactor, leading to the possibility of increased corrosion as the net molar ratio of catalyst to HF increases towards undesirable levels.

Since both the HF and organic feed might contain a small but significant amount of water (500 ppm with the HF, <50 ppm for the organic), a dehydrating agent such as SOCl$_2$ or COF$_2$ can be added in small amounts depending upon the amount of water present in these feeds. Water may act as a base in the system, decreasing the acidity of the system as measured on the Hammet scale. Since CO$_2$ and HCl have very similar vapor pressures, the use of dehydrating agents that also produce CO$_2$ are preferred because the CO$_2$ can then be easily vented off from the system along with the HCl at the top of column T-2.

The liquid accumulated in the reboiler of column T-2 is then be sent to column T-3, where the small amounts of more volatile organic intermediates can be separated from the HFC-245fa and HF. The HF/HFC-245fa enriched mixture that accumulates in the reboiler of column T-3 is then be sent to column T-4, where the HF/HFC-245fa is distilled away from higher boiling intermediates such as HCFC-244 and these higher boiling compounds are then sent back to the reactor at a rate equal to their accumulation in the reboiler.

The HF/HFC-245fa azeotrope-like composition can exit from the top of column T-4 and be vented into the HF extraction unit. The purified vapor leaving the top of this extraction column (the extraction column where concentrated H$_2$SO$_4$ is added in a counter-current fashion) is then be condensed and accumulated prior to any further purification steps—for example the removal of trace HF and trace amounts of unsaturated compounds, such as CF$_3$—CH═CClH and CF$_3$—CH═CFH. The resulting sulfuric acid-HF-fluorosulfonic acid solution leaving the bottom of the extraction column is then sent to a reboiler where the majority of the HF would be fractionally distilled away from the H$_2$SO$_4$—HSO$_3$F solution. The HF distillate can be condensed and recycled back to the HCFC synthesis reactor, while the HF depleted hot H$_2$SO$_4$ solution can be sent back to the extraction column T-4 after being cooled. The small amount of HFC-245fa and volatile unsaturated compounds contained in the distilled HF can also be included in this recycle stream. At this point, an HFC-245fa product having a purity at least about 99% is achievable.

EXAMPLES

The following non-limiting examples serve to illustrate certain aspects of the invention.

Example 1

Into a stirred 600 ml Hastelloy C autoclave was added 7.0 gram (0.032 gram-mole) of SbF$_5$ and 56.7 grams anhydrous HF (2.84 gram-moles). Next, 85.9 grams of HFC-245fa (0.642 mole) was added, followed by 48.5 grams (0.224 mole) of HCC-240fa. The mixture was then pressurized with N$_2$ to 170 psig, and then heated to about 120° C. over a 1 hour period and maintained at this temperature for an additional 2.5 hours. The bulk of the reaction took place in 34 minutes, as indicated by the amount of HCl byproduct vented from the system. The starting mole ratio of HF to HFC-245fa to SbF$_5$ was 88:19.8:1. Due to the evolution of HCl, the pressure rose significantly above the HF/HFC-245fa autogeneous pressure, and gas from the autoclave at a pressure greater than 400 psig was vented through a KOH scrubber/dryer and into a liquid nitrogen chilled collection cylinder over a 34 minute period. In this acid removing scrubber, a considerable amount of the product underwent a dehydrohalogenation reaction (forming the HFC-1234). The gas evolution ceased after the first hour, and was bled to atmospheric pressure at the end of the experiment. A total of 106.4 grams of organic was collected in the receiver with the following composition: 85.7% HFC-245fa, 9.4% HFC-1234, 2.52% HCFC-1233 and 1.48% HCFC-244 (the latter 3 compounds are intermediates in the synthesis of HFC-245fa). The net yield of product and formation of HFC-1234 byproduct, based upon the HCC-240 consumed, was 42.4% and 42.4%, respectively. There was no visible corrosion observed in this reaction, where the maximum temperature was 121° C. (560 psig. The net substitution of fluorine for chlorine on the organic feed was 98.1%. The reactor productivity was 2.5 lbs HFC-245fa/gallon-hr and 2.15 lbs HFC-1234/gallon-hr. When the HFC-245fa and HFC-1234 are treated as all HFC-245fa (HFC-245fa+KOH→HFC-1234+ KF+H$_2$O), the productivity would be near 5 lbs/gallon-hour.

Comparative Example 2

This example demonstrates the corrosion rate of a SbCl$_5$/HF system on equipment that can be used to produce HFC-245fa. Into a stirred Hastelloy C autoclave was added 299 parts SbCl$_5$ (1 mole) and 60 parts HF (3 mole). The mixture was heated to 80° C. for 4 hours in preparation for the addition of HCC-240fa and Cl$_2$, when HF was observed to be leaking from the autoclave. The corrosion rate was approximately 0.06 inches/hour on the baffle/thermowell, and even greater on the agitator blades, where the fluid velocities were greatest.

Example 3

A corrosion study was performed on an HF/SbF$_5$/HFC-245fa system at 90° C. upon various metals and alloys. Using a solution of 5 wt % SbF$_5$, 47.7 wt % HF and 47.3 wt % HFC-245fa, the corrosion rate for Hastelloy C, Inconel 600, Incoloy 825, Monel 400, SS 316 and C1018 carbon steel. The results of this example are provided in Table 1.

TABLE 1

| Materials of Construction | Corrosion Rate (mils/year) |
| --- | --- |
| Hastelloy C | 0 |
| Inconel 600 | 27 |
| Incoloy 825 | 9 |
| Monel 400 | 30 |
| SS 316 | 21 |
| C1018 carbon steel | 96 |

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A liquid-phase method of producing 1,1,1,3,3-pentafluoropropane comprising:
    (a) providing a catalytic solution comprising a fluorinated superacid catalyst at least partially dissolved in an azeotrope-like mixture of 1,1,1,3,3-pentafluoropropane and hydrogen fluoride; and
    (b) adding to said catalytic solution at least one non-fluorinated hydrochlorocarbon under conditions effective to convert at least a portion of said nonfluorinated hydrochlorocarbon to 1,1,1,3,3-pentafluoropropane.

2. The method of claim 1 wherein said non-fluorinated hydrochlorocarbons is selected from the group consisting of 1,1,1,3,3-pentachloropropane,1,3,3,3-tetrachloropropene and combinations thereof.

3. The method of claim 2 wherein said non-fluorinated hydrochlorocarbons comprises 1,1,1,3,3-pentachloropropane.

4. The method of claim 2 wherein said non-fluorinated hydrochlorocarbons comprises 1,3,3,3-tetrachloropropene.

5. The method of claim 1 wherein said fluorinated superacid catalyst comprises at least one compound selected from the group consisting of SbF$_5$, NbF$_5$, TaF$_5$, a mixture of TaF$_5$ and SnF$_5$ and combinations of two or more of these.

6. The method of claim 5 wherein said fluorinated superacid catalyst comprises SbF$_5$.

7. The method of claim 1 wherein at least a portion of said conversion step comprises conducting a reaction at a temperature of from about 60° C. to about 120° C.

8. The method of claim 1 wherein said effective conditions comprise maintaining said hydrogen fluoride and said non-fluorinated hydrochlorocarbons in a reaction mixture in a mole ratio of at least about 10:1.

9. The method of claim 8 wherein said hydrogen fluoride and said 1,1,1,3,3-pentafluoropropane in said reaction mixture are present in a mole ratio of not more than about 12:1.

10. The method of claim 8 wherein said hydrogen fluoride and said fluorinated superacid catalyst are present in a molar ratio of at least about 10:1.

11. The method of claim 1 wherein said method is a continuous process.

12. The method of claim 11 further comprising adding hydrogen fluoride to said catalytic solution as a component of a first feed stream and said non-fluorinated hydrochlorocarbon is added to said solution as a component of a second feed stream.

13. The method of claim 12 further comprising the step of recycling at least a portion of at least one of unreacted hydrochlorocarbons, hydrogen fluoride, and partially fluorinated organic intermediates from said liquid reaction system back into said solution as a recycle stream.

14. The method of claim 13 wherein said first and second feed streams and said recycle stream comprise a net molar feed ratio of hydrogen fluoride to hydrochlorocarbons of at least about 5:1.

15. The method of claim 12 further comprising the step of neutralizing at least a portion of water introduced into said reaction system via said first feed stream, second feed stream, or said catalytic solution, by contacting said water with a dehydrating agent selected from the group consisting of COCl$_2$, COF$_2$, and SOCl$_2$.

16. A method of producing a C2-C4 hydrofluorocarbon comprising:
    (a) providing a catalytic solution comprising C2-C4 hydrofluorocarbon, fluorinating agent, and a fluorinated superacid catalyst at least partially dissolved in said C2-C4 hydrofluorocarbon; and
    (b) adding to said catalytic solution at least one non-fluorinated hydrochlorocarbon under conditions effective to produce C2-C4 hydrofluorocarbon.

17. The method of claim 16 wherein said C2-C4 hydrofluorocarbon comprises 1,1,1,3,3-pentafluoropropane.

18. The method of claim 16 wherein said non-fluorinated hydrochlorocarbons is selected from the group consisting of 1,1,1,3,3-pentachloropropane,1,3,3,3-tetrachloropropene, and mixtures thereof.

19. The method of claim 16 wherein said fluorinated superacid catalyst comprises at least one compound selected from the group consisting of SbF$_5$, NbF$_5$, TaF$_5$, a mixture of TaF$_5$ and SnF$_5$, and combinations thereof.

20. The method of claim 16 wherein said fluorinating agent comprises HF.

21. The method of claim 16 wherein said effective conditions comprise contacting said catalytic solution with said at least one non-fluorinated hydrochlorocarbon at a temperature of from about 60° C. to about 120° C.

* * * * *